US012685600B1

(12) United States Patent
Schlenger et al.

(10) Patent No.: US 12,685,600 B1
(45) Date of Patent: *Jul. 21, 2026

(54) APPARATUS AND METHOD FOR TRACKING HAND-HELD SURGICAL TOOLS

(71) Applicant: Verdure Imaging, Inc., Stockton, CA (US)

(72) Inventors: Christopher Schlenger, Stockton, CA (US); Tamas Ungi, Kingston (CA)

(73) Assignee: Verdure Imaging, Inc., Stockton, CA (US)

( * ) Notice: Subject to any disclaimer, the term of this patent is extended or adjusted under 35 U.S.C. 154(b) by 244 days.

This patent is subject to a terminal disclaimer.

(21) Appl. No.: 18/387,191

(22) Filed: Nov. 6, 2023

Related U.S. Application Data

(63) Continuation of application No. 17/966,103, filed on Oct. 14, 2022, now Pat. No. 11,806,093.

(51) Int. Cl.
| | |
|---|---|
| *A61B 34/20* | (2016.01) |
| *A61B 34/10* | (2016.01) |
| *A61B 34/30* | (2016.01) |
| *A61B 90/00* | (2016.01) |

(52) U.S. Cl.
CPC ............. *A61B 34/20* (2016.02); *A61B 34/30* (2016.02); *A61B 2034/102* (2016.02); *A61B 2034/105* (2016.02); *A61B 2034/2055* (2016.02); *A61B 2090/364* (2016.02); *A61B 2090/378* (2016.02); *A61B 2090/3937* (2016.02)

(58) Field of Classification Search
CPC . A61B 34/20; A61B 34/30; A61B 2034/2055; A61B 2090/3937
See application file for complete search history.

(56) References Cited

U.S. PATENT DOCUMENTS

| | | | | |
|---|---|---|---|---|
| 9,232,934 | B2 * | 1/2016 | Hershey ............... | A61B 8/4245 |
| 11,534,138 | B2 * | 12/2022 | Sprung .................... | G06N 3/08 |
| 11,880,980 | B2 * | 1/2024 | Linguraru ................. | G06T 7/40 |
| 2013/0289406 | A1 * | 10/2013 | Schlenger ............ | A61B 8/5207 |
| | | | | 600/443 |
| 2015/0133785 | A1 | 5/2015 | Schlenger et al. | |

(Continued)

FOREIGN PATENT DOCUMENTS

JP          2014221175 A          11/2014

*Primary Examiner* — John D Li

(74) *Attorney, Agent, or Firm* — Bamert Regan PLLC

(57) ABSTRACT

Determining location and orientation of a hand-held surgical tool is provided. One embodiment captures first image data that includes images of a first optical target on the hand-held surgical tool and a second optical target on a patient. Location and orientation of the first optical target in a 3D space is determined based only on the first image data. Current location and orientation of the hand-held surgical tool in the 3D space determined based on the determined location and orientation of the first optical target and based on retrieved model data representing the hand-held surgical tool. Location of the second optical target in the 3D space is determined based on the first image data. Then, a location of the patient's tissue in the 3D space relative to the location and orientation of the hand-held surgical tool is determined based on the determined location of the patient's second optical target.

20 Claims, 4 Drawing Sheets

(56) References Cited

U.S. PATENT DOCUMENTS

2016/0199147 A1 *   7/2016   Shin ...................... A61B 90/37
                                                        600/411
2017/0360401 A1    12/2017   Rothberg et al.

* cited by examiner

APPARATUS AND METHOD FOR TRACKING HAND-HELD SURGICAL TOOLS

CROSS REFERENCE TO RELATED APPLICATION

This non-provisional application is a continuation of U.S. patent application Ser. No. 17/966,103, filed Oct. 14, 2022, titled "APPARATUS AND METHOD FOR TRACKING HAND-HELD SURGICAL TOOLS" and claims the benefit of the filing date of such application under 35 U.S.C. § 120, the entirety of which is hereby incorporated herein by reference.

BACKGROUND OF THE INVENTION

During medical interventions. There is a great need to be exact in the positioning of hand-held surgical tools relative to tissues that the practitioner is going to be interacting with. Typically, the practitioner concurrently views both the working end of the hand-held surgical tool and the viewable portion of tissue that the practitioner is interacting with. However, the practitioner may not be able to visually see some tissue of interest and/or portion or the working end of the hand-held surgical tool that are not exposed to view.

Various electronic devices and systems have been developed to provide visualization aids to the practitioner while they are using a hand-held surgical tool to interact with tissue of a patient. Some systems provide visualization of the position of the working end of the hand-held surgical tool by presenting images on a display that is viewable by the practitioner. Sensing location and orientation of the working end of the hand-held surgical tool is typically done using ultrasound devices, computed tomography (CT) scanning devices, x-ray devices, fluoroscopy scanning devices, and/or magnetic resonance imaging (MRI) system. Each of the modalities comes with its own limitations. For example, X-ray machines, MRI machines and CT scanning machines are expensive to acquire and to use. X-ray images present graphical information on a limited two-dimensional-plane. MRI is unsatisfactorily slow and supplies low resolution images of bone structures and are not very practical in an operating theater or during procedures in outpatient setting.

Further, X-ray imaging, fluoroscopy and CT scanning use ionizing radiations (X-rays) that may be harmful to the patient and the practitioner who is performing a surgical procedure in the surgical theater. The longer the surgical procedure takes, the more potentially harmful radiation both the patient and the practitioner will be subjected to. For example, a patient that is getting an epidural injection in the spine will have to undergo a video fluoroscopy for an extended period of time. The practitioner may have to wear cumbersome lead shielding. The patient will also have to use a suitable lead shield. Further, the fluoroscope is usually exceptionally large and can leave only a small space available for the practitioner to work. Intra-operative CT such as cone beam will have similar downsides.

Other less potentially harmful electronic scanning systems and devices are available for acquiring patient information. For example, ultrasound devices project sound waves into the patient and detect returning sound wave echoes that are used to generate an image, referred to as a sonogram image. Ultrasound devices used in ultrasonographic systems produce sound waves at a frequency above the audible range of human hearing, which is approximately 20 kHz. Sound waves between 2 and 18 MHz are often used for ultrasound medical diagnostic applications. At present, there are no known long-term side effects from interrogating the human body with ultrasound waves.

However, an ultrasound scan can cover only a relatively small part of the patient's body with each scan. Further, the sonogram is a relatively narrow image, covering a relatively small cross-section of only a few inches. And objects found in the sonogram image may often be blurry. For example, five hundred to one thousand sonogram images must be captured to acquire enough image data for analysis of a full human spine. Accordingly, legacy ultrasound scanners are inadequate for acquiring image information for the patient's body when a large area of the human subject must be examined, such as the patient's spine, because the sonogram images are too small, and many sonogram images cannot be easily analyzed to arrive at any meaningful information about the condition of the examined patient.

There is also a problem with the differentiation of the tissue that is viewed in a sonogram image. That is, it is exceedingly difficult for the practitioner to tell which tissue they are viewing in a sonogram image. Typically, when a surgical procedure is performed on area near the spine, for example, the ultrasound system will only provide two dimensional (2D) ultrasound images. Even if real-time acquired sonogram images provide visual information that indicates the current location and orientation of a hand-held surgical tool during the surgical procedure, the practitioner still will have difficulty identifying some types of tissue in a presented sonogram image. Further, the practitioner will have difficulty identifying the location and/or orientation of the working end of the hand-held surgical tool with respect to the tissue (because the tissue is difficult to identify in a 2D sonogram image).

The inventors have created an ultrasonagraphic system that is operable to acquire sonogram information from a series of ultrasonic scans of a patient, as disclosed in U.S. Pat. Nos. 9,675,321 and 9,713,508, which are both incorporated by reference herein in their entirety. In practice, a series of time indexed ultrasound scans are taken over a portion of interest on the patient which has their underlying bone structure or other ultrasound discernable organ that is under examination. Location and orientation of the ultrasound scanner, and location of the scanned portion of the patient, are precisely identifiable in the time indexed sonogram images that are acquired from the sonogram scanner of the patient during the scanning process. The data from the series of acquired time indexed sonogram scans are synthesized into a single data file that is used to generate a three-dimensional (3D) image and/or 3D model of the underlying bone structure or organ of the examined patient, referred herein as a tissue model. However, this system is unsuitable for an actual surgical procedure since the 3D model of the tissue of interest (bone and/or organs of the patient) because the numerous individual sonogram scans used to generate a 3D tissue model must be acquired before initiation of the surgical procedure. The ultrasonagraphic system disclosed in U.S. Pat. Nos. 9,675,321 and 9,713,508 was not designed to sense location and orientation of a hand-held surgical tool during a surgical procedure.

Accordingly, there is a need in the arts to more effectively acquire image data that is presentable to a practitioner in real-time indicting current location and orientation of a hand-held surgical tool relative to the tissue of a human subject during a surgical procedure.

SUMMARY OF THE INVENTION

Embodiments of the hand-held surgical tool tracking system provide a system and method for tracking location and orientation of a hand-held surgical tool being manipulated by a practitioner to interact with tissue of a patient. Example embodiments determine location and orientation of a hand-held surgical tool by capturing image data that includes images of at least a first detectable target on the hand-held surgical tool and a second detectable target on the patient. Location and orientation of the first detectable target in a 3D space is determined based on the image data. Current location and orientation of the hand-held surgical tool in the 3D space determined based on the determined location and orientation of the first detectable target and based on retrieved model data representing the hand-held surgical tool. Location of the second detectable target in the 3D space is determined based on the image data. Then, a location of the patient's tissue in the 3D space relative to the location and orientation of the hand-held surgical tool is determined based on the determined location of the patient's second detectable target. In some embodiments, relative location of the hand-held surgical tool relative to a patient's tissue is determined. Then a composite image showing the hand-held surgical tool and an image of the tissue (based on a predefined model of the tissue) is presented on a 2D and/or 3D display.

BRIEF DESCRIPTION OF THE DRAWINGS

The components in the drawings are not necessarily to scale relative to each other. Like reference numerals designate corresponding parts throughout the several views.

FIGS. 1A-1E are figures of various types of hand-held surgical tools with one or more detectable targets at known locations on the surface of the hand-held surgical tool.

DETAILED DESCRIPTION OF THE PREFERRED EMBODIMENT

Figures 1A, 1B, 1C, 1D, 1E:
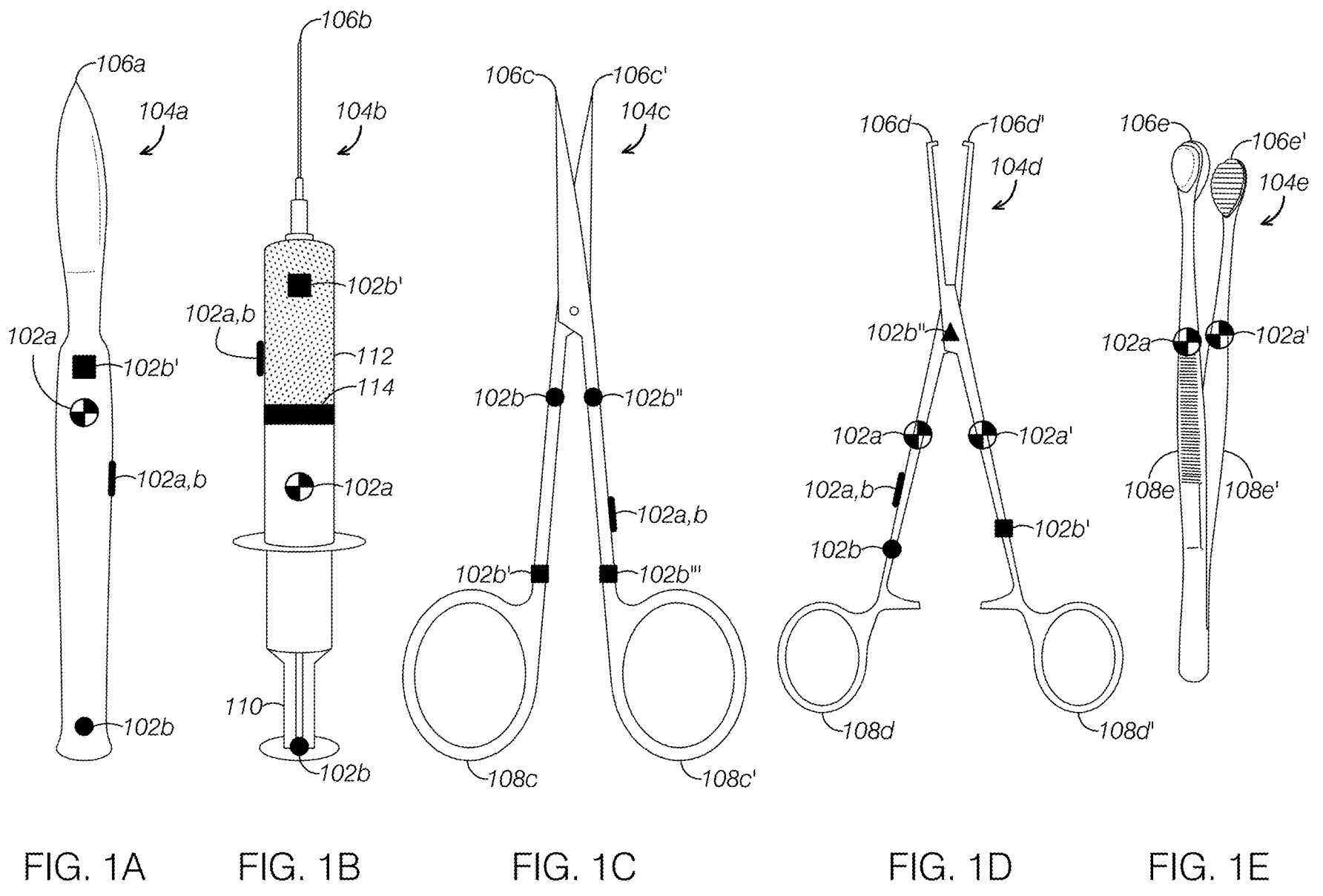
Figure 2:
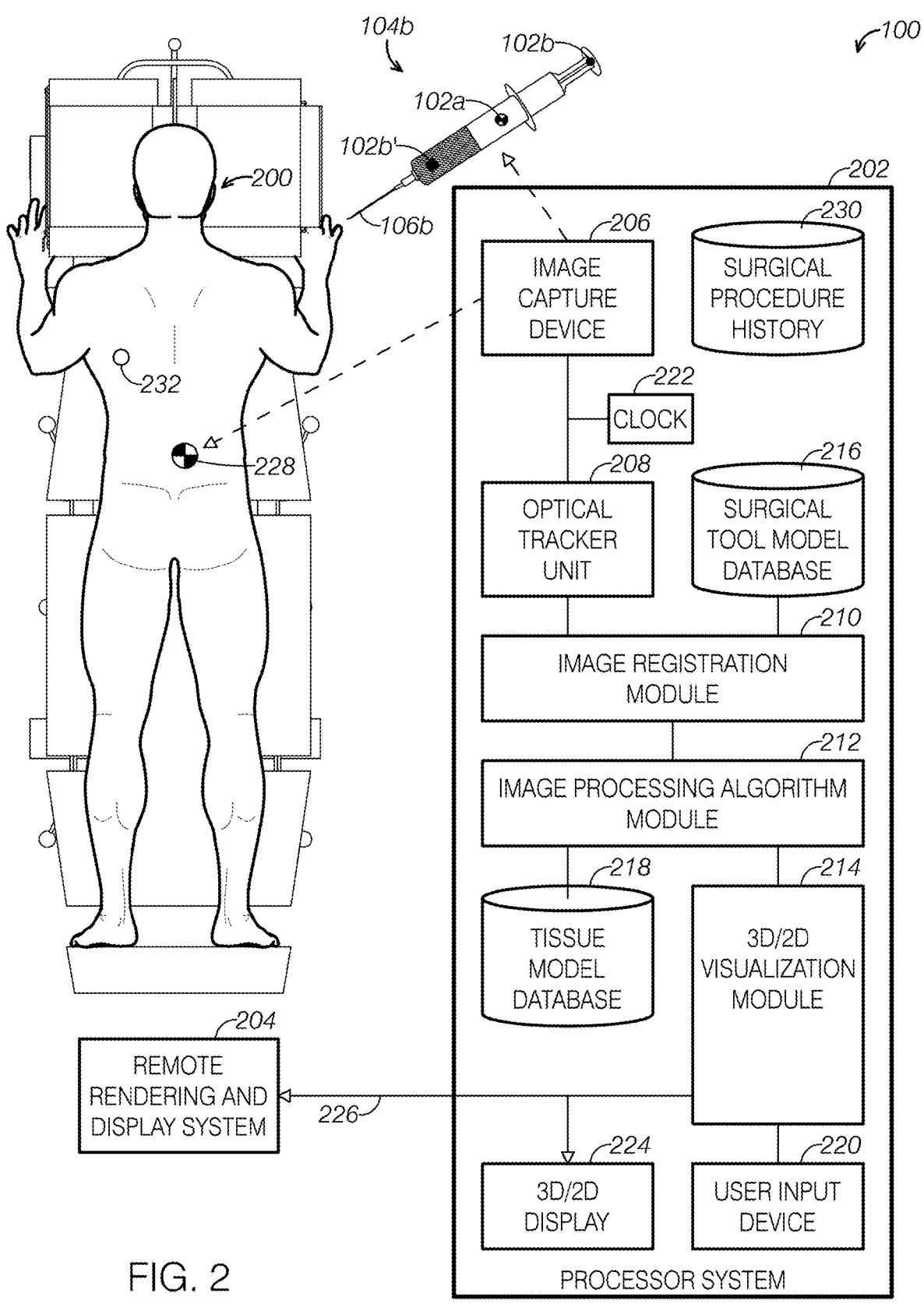
FIG. 2 is a schematic view of a hand-held surgical tool tracking system for assisting a practitioner performing a procedure on a human subject.

FIGS. 1A-1E are figures of various, non-limiting example types of hand-held surgical tools with one or more detectable targets 102a, 102b at known locations on the surface of the hand-held surgical tool 104a-e. In a preferred embodiment, the detectable targets 102a, 102b are optically detectable, though the detectable targets 102a, 102b may be detectable using non-optical systems. FIG. 2 is a schematic view of a hand-held surgical tool tracking system 100 for assisting a practitioner performing a surgical procedure on a human subject 200 (interchangeably referred to herein as a patient 200).

During the surgical procedure, embodiments of the hand-held surgical tool tracking system 100 determine location and orientation in three-dimensional (3D) space of the hand-held surgical tool 104, and in particular, the working end (tool end) of the hand-held surgical tool 104. Accordingly, the location and orientation in the 3D space of the hand-held surgical tool 104 that is being manipulated by the practitioner during a surgical procedure is determinable in real-time or near real-time. Based on a predetermined model of the tissue of interest that is being operated on by the practitioner, a real-time or near real-time rendering and presentation of an image showing the interaction of the working end 106 of the hand-held surgical tool 104 with a two-dimensional (2D) or three dimensional (3D) model of the tissue of the patient 200 is presented on a display. Accordingly, the practitioner may intuitively understand the actual location of the working end 106 of the hand-held surgical tool 104 with respect to the tissue that is being operated on.

The presented image of the tissue and the hand-held surgical tool 104 may be presented as a 2D image and/or a 3D image. Is some embodiments, the practitioner (or an assistant) wear virtual reality glasses to view the 3D image of the working end 106 of the hand-held surgical tool 104 interacting with the tissue of interest. Multiple displays may concurrently present the 2D image and/or the 3D image so that other parties may view the ongoing surgical procedure. Further, the time sequenced 2D images and/or a 3D images may be saved for later review.

The disclosed systems and methods for or assisting a practitioner performing a procedure on a human subject 200 (FIG. 2) using the hand-held surgical tool tracking system 100 will become better understood through review of the following detailed description in conjunction with the figures. The detailed description and figures provide examples of the various inventions described herein. Those skilled in the art will understand that the disclosed examples may be varied, modified, and altered without departing from the scope of the inventions described herein. Many variations are contemplated for different applications and design considerations, however, for the sake of brevity, each and every contemplated variation is not individually described in the following detailed description.

Throughout the following detailed description, a variety of examples the hand-held surgical tool tracking system 100 are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

The following definitions apply herein, unless otherwise indicated.

"Substantially" means to be more-or-less conforming to the particular dimension, range, shape, concept, or other aspect modified by the term, such that a feature or component need not conform exactly. For example, a "substantially cylindrical" object means that the object resembles a cylinder, but may have one or more deviations from a true cylinder.

"Comprising," "including," and "having" (and conjugations thereof) are used interchangeably to mean including but not necessarily limited to, and are open-ended terms not intended to exclude additional elements or method steps not expressly recited.

Terms such as "first", "second", and "third" are used to distinguish or identify various members of a group, or the like, and are not intended to denote a serial, chronological, or numerical limitation.

"Coupled" means connected, either permanently or releasably, whether directly or indirectly through intervening components. "Secured to" means directly connected without intervening components.

"Communicatively coupled" means that an electronic device exchanges information with another electronic device, either wirelessly or with a wire based connector, whether directly or indirectly through a communication network. "Controllably coupled" means that an electronic device controls operation of another electronic device.

"Real-time" means that real-time is instant, whereas "near real-time" is delayed by some amount of time (whether that's by a few milliseconds or even less.

In the various embodiments, like reference numerals represent like components. For example, the reference numeral 104 may be used to generically represent any hand-held surgical tool, and reference numeral 104a may be used to identify a specific hand-held surgical tool, such as the example scalpel 104a (FIG. 1A).

Optical targets 102 (interchangeably referred to herein as detectable targets 102) may be any conventional, specially developed, or later developed optical target that is discernable by an optical tracking system of the hand-held surgical tool tracking system 100. In some examples, the optical targets 102 may extend in three dimensions about a three coordinate axis and include distinct optical target portions representing each axis. In other examples, the optical target 102 may extend in three dimensions about six axes and include distinct optical targets representing each of the six axes. Optical targets 102 are discernably to the human eye and are discernable in a captured image (photographic image or video image).

The detectable targets 102 may be active, such as by emitting (or reflecting) electromagnetic signals or other energy signals from the detectable target 102. Or the detectable target 102 may be passive, such as a retro-reflective marker that reflects radiation energy emitted by some inter-action device. Such active or passive targets 102 are generically described herein as detectable targets 102 for brevity, though such detectable targets 102 may not be optically detectable by an image capture device. Any suitable detectable target 102 that is now known or later developed is intended to be within the scope of this disclosure and to be protected by the accompanying claims.

In the various embodiments, each of the detectable targets 102 are uniquely identifiable. In some embodiments, a visible characteristic of an optical target (or at least one optical target) can be compared to known identification characteristics of the optical target so a particular optical target 102 is identifiable. For example, the shape of the optical targets 102 may be different. If the optical targets 102 are small marks, such as dots or the like, the number of marks for each of the optical targets 102 may identify that particular optical target 102. A unique alpha-numeric identifier may be located proximate to or on the optical targets 102. Active detectable targets 102 may emit different signals with identifier information. In embodiments that employ only a single optical target 102, that single optical target 102 is inherently identifiable.

As conceptually illustrated in FIG. 2, the non-limiting example embodiment of the hand-held surgical tool tracking system 100 comprises a processor system 202, at least one hand-held surgical tool 104, and an optional remote rendering and display system 204. The processor system 202 comprises at least one image capture device 206, a target tracker unit 208, an image registration module 210, an image processing algorithm module 212, a 3D/2D visualization module 214, a surgical tool database 216, a tissue model database 218, and a user input device 220. Some embodiments include an optional clock 222. Some embodiments may include an optional display 224. Any suitable processor system now known or later developed is intended to be included withing the scope of this disclosure and to be protected by the accompanying claims. In some embodiments, the processor system 202 may be communicatively coupled to the remote rendering and display system 204 via a wire-based or wireless connection 226. Other embodiments of the hand-held surgical tool tracking system 100 may include some, or may omit some, of the above-described components. Further, additional components not described herein may be included in alternative embodiments.

In an example embodiments, the discernable targets 102 are optical targets 102. Here, the optical targets are discernable to a human viewer and are detectable in a photographic image. The image capture device 206 is still or video camera device, and the acquired image data are still image photograph data or photographic video data.

FIGS. 1A-1E represent a non-limiting selection of example hand-held surgical tools 104a-104e. Any particular hand-held surgical tool may include one or more detectable targets 102. Each type of hand-held surgical tool 104 is uniquely identifiable. An identifier of the hand-held surgical tool 104 may be located on each hand-held surgical tool 104. The identifier may be an alpha-numeric identifier, a bar or QR code, or the like that can be identified to the hand-held surgical tool tracking system 100.

For example, a captured image or a scan of the hand-held surgical tool 104 may be analyzed by the hand-held surgical tool tracking system 100 to determine the identifier of the hand-held surgical tool 104 using any suitable alphanumeric text character recognition algorithm. Alternatively, or additionally, a radio frequency identifier tag (RFID) may be placed on the hand-held surgical tool 104 and/or its packaging that can be read by an RFID reader provisioned within the hand-held surgical tool tracking system 100 or that is communicatively coupled to the hand-held surgical tool tracking system 100. In some embodiments, an object recognition algorithm may be used to identify the surgical tool 104 based on captured image data. Alternatively, or additionally, the practitioner or another party may manually specify the identifier of the hand-held surgical tool 104 to the hand-held surgical tool tracking system 100 (such as if the specification is entered using a keyboard, if entered using a touch sensitive screen, or is spoken to an audible detection and recognition system). Once the particular hand-held surgical tool 104 has been identified to the hand-held surgical tool tracking system 100, then hand-held surgical tool model data corresponding to the identified surgical tool 104 (a model of the hand-held surgical tool model) can be retrieved so that the processor system 202 can determine the precise location and orientation of the identified hand-held surgical tool 104, and in particular the working end 106 located at the distal end of the hand-held surgical tool 104, during the surgical procedure.

Returning to FIG. 1A, the particular hand-held surgical tool 104 is appreciated to be a scalpel 104a. The scalpel 104a has a working end 106a (interchangeably referred to herein as a tool 106a or blade 102a) that is understood by one skilled in the art to be the cutting edge or blade 1061 located at the distal end of the scalpel 104a. Prior to use of the scalpel 104a during the surgical procedure, one or more identifiable optical targets 102 are placed at known locations (or are fabricated at the known locations) on the surface of the scalpel 104*a* in the various preferred embodiments. Preferably, each of the optical targets 102 will be uniquely identifiable.

A variety of different types of detectable targets 102 may be used in the various embodiments. A non-limiting first type is the example optical target 102*a* that has a plurality of distinct optical target portions. When the optical target 102*a* is viewed in a captured image (or more precisely, when image data corresponding to the optical target 102*a* is analyzed by the processor system 202), the location and orientation of that optical target 102*a* can be precisely determined based on image characteristics of the image target portions (i.e., relative location to each other). Since the orientation and location of the identified optical target 102*a* is known with respect to all portions of the scalpel 104*a*, and in particular to the location of the blade 106*a*, the precise location and orientation of the blade 106*a* in the 3D space can be determined using a stored model corresponding to the scalpel 104*a*.

In this non limiting example conceptually illustrated in FIG. 1A, a model of the scalpel 104*a* with data corresponding to the example optical target 102 has been predetermined and stored. The location of each portion of the scalpel 104*a* relative to the optical target 102*a*, and in particular the precise location and orientation of the blade 106*a* to the optical target 102*a*, is represented in the model data of the scalpel 104*a*. When the acquired image data of the scalpel 104*a* is correlated with the scalpel model data, embodiments of the hand-held surgical tool tracking system 100 determines the precise location and orientation of the scalpel 104*a*, and in particular the precise location and orientation of the blade 106*a*, in 3D space.

Alternatively, or additionally, a plurality of optical targets 102*b* may be located on the surface of the hand-held surgical tool 104. Such optical targets 102*b* may be simple marks, such as one or more small colored dots, squares, triangles, stars, or the like, that can be identified in the image data acquired by the image capture device 206. Differing colors of and/or patterns on the mark may be used. Any suitable shape, color and/or pattern may be used in the various embodiments, particularly for mark identification purposes. The precise location and identity of each of the identifiable optical targets 102*b* on the surface of the hand-held surgical tool 104 is known using a stored model corresponding to the scalpel 104*a*. With respect to the scalpel 104*a*, two optical targets 102*b* and 102*b'* are illustrated (wherein a characteristic of the optical target 102*b* is different from the optical target 102*b'* for identification purposes). Once at least two optical targets 102*b* are identified in the captured image data, then the precise location and orientation of the scalpel 104*a* in 3D space can be computed (determined) by the processor system 202 based on the identified relative location of the at least to optical targets 102*b* with respect to each other. Additional optical markers102*b* may be used to improve accuracy of the determined location and orientation of the scalpel 104*a*.

In this non limiting example conceptually illustrated in FIG. 1A, a model of the scalpel 104*a* with the example optical targets 102*b* and 102*b'* has been predetermined and stored. The location of each portion of the scalpel 104*a* relative to the optical targets 102*b* and 102*b'*, and in particular the precise location and orientation of the blade 106*a* to the optical target 102*b* and/or 102*b'*, is represented in the model data of the scalpel 104*a*. When the acquired image data of the scalpel 104*a* is correlated with the scalpel model data, embodiments of the hand-held surgical tool tracking system 100 determines the precise location and orientation of the scalpel 104*a*, and in particular the precise location and orientation of the blade 106*a*, in 3D space. One skilled in the art appreciates that the optical targets 102*b* and 102*b'* are preferably uniquely identifiable so that the location and orientation of working end 106 of the hand-held surgical tool 104 is determinable. (If the optical targets 102*b* and 102*b'* are not identifiable from each other, it is possible that an incorrect orientation and location of the surgical tool 104 could be determined. Employing uniquely identifiable optical targets 102*b* and 102*b'* solves this potential problem.)

In FIG. 1B, the particular hand-held surgical tool 104 is appreciated to be a generic syringe 104*b*. The syringe 104*b* has a working end 106*b* that is understood by one skilled in the art to be the tip of a needle (located at the distal end of the syringe 104*b* that is used to puncture a patient for injecting medicine or drawing tissue samples. Prior to use of the syringe 104*b* during the surgical procedure, one or more identifiable optical targets 102*a* and/or 102*b* are placed at known locations (or are fabricated at the known locations) of the surface of the syringe 104*b* in the various preferred embodiments. Preferably, each of the optical targets 102 will be uniquely identifiable. (It is appreciated that one or more optical targets 102*a*, and/or three or more optical targets 102*b*, might be used in other embodiments.)

Additionally, some embodiments may be configured to determine the relative distance between the optical targets 102*b*, 102*b'* during the surgical procedure. For example, the optical target 102*b* may be located on a plunger 110 of the syringe 104*b*. The second optical target 102*b'* may be located on the barrel 112 of the syringe 104*b* The change in distance between the optical targets 102*b*, 102*b'* during the course of the surgical procedure may then be used to precisely compute a travel distance of the barrel seal 114 that is at the distal end of the plunger 110. Since the volume of the barrel 112 is known and the volume information is stored as part of the syringe model data, the volume of medicine injected out from the syringe 104*b* and/or the amount of tissue collected within the syringe 104*b* may be precisely determined based on the determined travel distance of the barrel seal 114. This information may be presented to the practitioner on a real-time basis during the surgical procedure.

In FIG. 1C, the particular hand-held surgical tool 104 is appreciated to be a generic surgical scissor 104*c*. The surgical scissor 104*c* has a first working end 106*c* and a second working end 106*c'* (located at the distal end of the surgical scissor 104*c*) that is understood by one skilled in the art to be the cutting end that is used to cut tissue during a surgical procedure. Prior to use of the surgical scissor 104*c* during the surgical procedure, a plurality of identifiable optical targets 102 are placed at known locations (or are fabricated at the known locations) of the surface of the surgical scissor 104*c* in the various preferred embodiments. Preferably, each of the optical targets 102 will be uniquely identifiable.

One skilled in the art appreciates that for precise determination of the location of the cutting edges of the surgical scissor 104*c*, the precise location of each working end 106*c*, 106*c'* must be individually determined. To enable this determination of the precise location and orientation of the surgical scissor 104*c* and the working ends 106*c*, 106*c'* during the surgical procedure, each of the two first surgical tool members 108*c* and 108*c'* of the surgical scissor 104*c* must each have their own optical targets 102. In the non-limiting example embodiment illustrated in FIG. 1C, the first surgical tool member 108*c* includes a first optical target 102*b* and a second optical target 102*b'*. The second surgical tool member 108c' includes a third optical target 102b" and a fourth optical target 102b'''. The determined location of the optical targets 102b", 102b''' may be used to determine the precise location and orientation of the working end 106c. Similarly, the determined location of the optical targets 102b, 102b' may be used to determine the precise location and orientation of the working end 106c'. Alternatively, or additionally, the relative separation between the optical targets 102b and 102b", and/or the optical targets 102b' and 102b''', may be used in the computations.

Alternatively, or additionally, a plurality of optical targets 102a (not shown) may be used to track the members 108c, 108c'. Three optical targets 102b may be used (see FIG. 1D, for example).

In practice, the surgical scissor 104c may be closed at some point during the surgical procedure wherein the working ends 106c, 106c' are adjacent to and/or are in contact with each other. At another point during the surgical procedure, the surgical scissor 104c may be opened such that the working ends 106c, 106c' are separated from each other by a determinable distance so that the practitioner can insert the working ends 106c, 106c' around the tissue that is to be cut. Further, as the practitioner is cutting the tissue of interest, the working ends 106c, 106c' are moving towards each other in a cutting motion. Accordingly, determination of the precise location and orientation of the surgical scissor 104c, and in particular the working ends 106c, 106c', is determinable in real-time or near real-time.

In FIG. 1D, the particular hand-held surgical tool 104 is appreciated to be a generic surgical clamp 104d. The surgical clamp 104d has a first working end 106d and a second working end 106d' (located at the distal end of the surgical clamp 104d) that is understood by one skilled in the art to be clamps that are used to clamp tissue during a surgical procedure. Prior to use of the surgical clamp 104d during the surgical procedure, a plurality of identifiable optical targets 102 are placed at known locations (or are fabricated at the known locations) of the surface of the surgical clamp 104d in the various preferred embodiments. Preferably, each of the optical targets 102 will be uniquely identifiable.

Similar to the above-described surgical scissor 104c, one skilled in the art appreciates that for precise determination of the location of the clamping ends of the surgical clamp 104d, the precise location of each working end 106d, 106d' must be individually determined. For example, the surgical clamp 104d may be opened such that the working ends 106d, 106d' are separated from each other by a determinable distance so that the practitioner can insert the working ends 106d, 106d' around the tissue that is to be clamped. At another point during the surgical procedure, the surgical clamp 104d may be later closed during the surgical procedure wherein the working ends 106d, 106d' are adjacent to and/or are in contact with each other to clamp the tissue of interest. Further, as the practitioner is clamping the tissue of interest, the working ends 106c, 106c' are moving towards each other in a clamping motion. Accordingly, determination of the precise location and orientation of the surgical clamp 104d, and in particular the working ends 106d, 106d', is determinable in real-time or near real-time.

In the non-limiting example of the surgical clamp 104d, to enable the determination of the precise location and orientation of the surgical clamp 104d and the working ends 106d, 106d' during the surgical procedure, each of the two surgical tool members 108d and 108d' of the surgical clamp 104d are conceptually illustrated as having their own optical target 102a. In the non-limiting example embodiment illustrated in FIG. 1D, the first surgical tool member 108d includes a first optical target 102a. The second surgical tool member 108d' includes a second optical target 102b'. Once the precise location and orientation of each arm 108d, 108d' is determined, the precise location and orientation of the surgical clamp 104d and its associated working ends 106d, 106d' can be determined by the processor system 202.

Alternatively, or additionally, to enable the determination of the precise location and orientation of the surgical clamp 104d and the working ends 106d, 106d' during the surgical procedure, each of the two surgical tool members 108d and 108d' of surgical clamp 104d are conceptually illustrated as having their own optical targets 102b and 102b', respectively. A third optical target 102b" is located at the hinge of the surgical clamp 104d (where the first surgical tool member 108d is hinge-ably coupled to the second surgical tool member 108d"). Here, the precise location and orientation of the first surgical tool member 108d (first arm 108d) can be determined based on the determined location of the first optical target 102b and the hinge optical target 102b". Similarly, the precise location and orientation of the second surgical tool member 108d' can be determined based on the determined location of the first optical target 102b' and the hinge optical target 102b". Once the precise location and orientation of each surgical tool member 108d, 108d' is determined, the precise location and orientation of the surgical clamp 104d and its associated working ends 106d, 106d' can be determined by the processor system 202 in real-time or near real-time.

As noted herein, a hand-held surgical tool 104 may have only one type of detectable target 102 or a plurality of different types of detectable targets 102. For example, the non-limiting surgical clamp 104d uses two different types of optical targets 102a and 102b. Other embodiments of the surgical clamp 104d may use only one of the types of the optical targets 102 (and/or may use other types of optical targets 102). Use of different types of optical targets 102 enables the same hand-held surgical tool 104 to be used with different embodiments of the hand-held surgical tool tracking system 100 that employ different image processing algorithms modules 212 that are configured to identify a particular type of optical target 102. This feature of detectable targets 102 may be used on any hand-held surgical tool 104.

In FIG. 1E, the particular hand-held surgical tool 104 is appreciated to be a generic surgical tweezer 104e. The surgical tweezer 104e has a first working end 106e and a second working end 106e' (located at the distal end of the surgical tweezer 104e) that is understood by one skilled in the art to be the grasping tool end that is used to grasp tissue during a surgical procedure. Prior to use of the surgical tweezer 104e during the surgical procedure, a plurality of identifiable optical targets 102 are placed at known locations (or are fabricated at the known locations) of the surface of the surgical clamp 104d in the various preferred embodiments. Preferably, each of the optical targets 102 will be uniquely identifiable.

In the non-limiting example of the surgical tweezer 104e, to enable the determination of the precise location and orientation of the surgical tweezer 104e and the working ends 106e, 106e' during the surgical procedure, each of the two surgical tool members 108e and 108e' of the surgical tweezer 104e are conceptually illustrated as having their own optical target 102a, 102a', respectively. Once the precise location and orientation of each surgical tool member 108e, 108e' is determined, the precise location and orientation of the surgical tweezer 104*e* and its associated working ends 106*e*, 106*e'* can be determined by the processor system 202.

One skilled in the arts appreciates that there are a variety of different types of hand-held surgical tools that might be used by a practitioner during a surgical procedure. Accordingly, the example hand-held surgical tools 104 of FIGS. 1A-1E are intended to represent only a sampling of possible hand-held surgical tools that may be tracked using detectable targets 102. Further, some hand-held surgical tools may have working ends locate at both the proximal and distal ends of the hand-held surgical tool (such as encountered in the dentistry arts). All such manually manipulated hand-held surgical tools 104 now known or later developed are intended to be withing the scope of this disclosure and to be protected by the accompanying claims.

Some embodiments may employ a plurality of different detectable targets 102*a*, 102*b* located on other surfaces of the hand-held surgical tool 104. For example, detectable targets 102*a*, 102*b* may be located on the opposing surface of the scalpel 104*a* and or on the side surfaces of the scalpel 104*a*. For example, multiple detectable optical targets 102*a*, 102*b* may be on the same surface of the hand-held surgical tool 104 in case the practitioner's hand or another object blocks a view of the hand-held surgical tool 104 by the image capture device 206 during the surgical procedure. Accordingly, a sufficient number of detectable optical target(s) 102*a*, 102*b* will always be discernable in an image that is being captured by the image capture device 206 (FIG. 2). Therefore, the practitioner does not need to worry about how they are grasping the hand-held surgical tool 104 during the surgical procedure.

As noted herein, the precise location and orientation of the working end 106 of any hand-held surgical tool 104 is precisely determined based on a determined location of the one or more detectable targets 102. One skilled in the arts understands how such location and orientation calculations are performed to identify the precise location and orientation of the hand-held surgical tool 104 in a known 3D space based on the determined locations of detectable targets 102, such as the example optical targets 102*a*, 102*b*. Accordingly, such geometry calculations are not described herein for brevity.

Prior to performing a surgical procedure using any one of the available hand-held surgical tools 104, the precise location of each detectable target 102 on the surface of the hand-held surgical tool 104 is known. The known location of each detectable target 102 may be based on design specifications. During manufacture, each of the detectable targets 102 are fabricated at their precisely known locations and/or orientations. An unexpected advantage of incorporating the detectable target(s) 102 as part of a manufactured hand-held surgical tool 104 is that hundreds, even thousands, of like hand-held surgical tools 104 may be manufactured and distributed to different sites. If the site of the surgical procedure has an embodiment of the hand-held surgical tool tracking system 100, then the precise location and orientation of the hand-held surgical tool 104 can be determined during the surgical procedure. However, if the site does not have an embodiments of the hand-held surgical tool tracking system 100, the hand-held surgical tool 104 still may be used by the practitioner to perform the surgical procedure in a conventional manner.

Alternatively, or additionally, the detectable target(s) 102 may be placed onto the surface of the hand-held surgical tool 104 after its manufacture. Here, each detectable target 102 is secured to the surface of the hand-held surgical tool 104 at a precisely known location and/or orientation (using an adhesive, by painting, or the like). Preferably, the detectable target(s) 102 are secured to many of the like hand-held surgical tools 104 at identical locations prior to distribution to the different sites where a surgical procedure is to be performed.

An unexpected advantage of distributing many like hand-held surgical tools 104, each with their detectable targets 102 at the identically same location and/or orientation on the hand-held surgical tool 104, is that a single model of that particular hand-held surgical tool 104 may be generated and stored. The hand-held surgical tool model data may be saved locally at the surgical instrument model database 216 (FIG. 2) and/or remotely in a remote database.

For example, thousands of scalpels 104*a* may be manufactured and distributed to many different surgical sites (e.g., hospitals, clinics, etc.). If the surgical site where the surgical procedure is being performed is provisioned with an embodiment of the hand-held surgical tool tracking system 100, then the practitioner (or their assistant) can use any of the available scalpels 104*a* during the surgical procedure. Further, different types of hand-held surgical tools 104 may be used by the practitioner during the surgical procedure since each different type of hand-held surgical tool 104 is readily identifiable by embodiments of the hand-held surgical tool tracking system 100.

Yet another unexpected advantage is that any particular type of hand-held surgical tool 104 with precisely located detectable targets 102 is that different manufacturers of the particular type of hand-held surgical tool 104 may provide their proprietary tool 104 to the practitioners for various surgical procedures. If the manufacturers produce identical hand-held surgical tools 104, a single model may represent the hand-held surgical tool 104 that has been distributed by different manufacturers. In the event that there are differences between a particular type of hand-held surgical tool 104 being produced by different manufacturers, then a hand-held surgical tool model may be generated and saved for each particular manufacturer.

Alternatively, or additionally, the detectable targets 102 may be secured to a hand-held surgical tool 104 of interest (using a suitable adhesive or paint) by the practitioner or another party prior to use. For example, one or more images of the hand-held surgical tool 104 are captured after manual placement of the optical targets 102 during a hand-held surgical tool calibration process. Embodiments of the hand-held surgical tool tracking system 100 then analyze the acquired image data to identify the precise location and/or orientation of the optical target(s) 102, and the location of the working end(s) 106 of the hand-held surgical tool 104. Then, embodiments of the hand-held surgical tool tracking system 100 may generate a calibrated model of the photographed hand-held surgical tool 104. An unexpected advantage of this embodiment is that any hand-held surgical tool 104 of interest may be fitted with one or more optical targets 102, and then may be used during the surgical procedure.

In the conceptual illustration of FIG. 2, the patient 200 is laying on their stomach on an operating table or the like. Hypothetically, assume that the practitioner (not shown) is intending to insert the needle 106*b* (the working end) of the syringe 104*b* into an intended location within the patient's spine (not shown). Although the precise location and orientation of the syringe 104*b* in the 3D space is determinable, it is not possible to know the exact location of the patient's tissue of interest (here, the patient's spine) because of the patient's covering skin.

Accordingly, a calibration of patient 200 is required before initiation of the surgical procedure. In the conceptual example illustrated in FIG. 2, at least one detectable target 228 is placed on the patient 200 or at another suitable location proximate to the patient 208. If an optical target 228 is used, an image capture device 206 acquires an image of the optical target 228, and then determines the precise location and orientation of the optical target 228. Since the optical target 228 is located at a known location with respect to the patient (proximate to), the location of the tissue of interest may be computed based on information that is known about the patient 200. That is, a location relationship between a tissue of interest of the patient 200 and the predefined location of the detectable target 228 is known. Once the location of the tissue of interest is known, then the relative location relationship between the tissue and the hand-held surgical tool 104 can be determined during the course of the surgical procedure. This patient tissue calibration approach may be adequate if the tissue of interest is visible on the surface of the patient 200, and/or if a high degree of precision is not needed. For example, if the tissue of interest is a mole or the like on the skin of the patient 200, this patient tissue calibration technique may be adequate. Location of the tissue of interest may be enhanced by embodiments of the hand-held surgical tool tracking system 100 using object recognition techniques. For example, an image of the skin of the patient may be analyzed to identify and locate the mole on the patient's skin.

However, one skilled in the art appreciates that the above-described patient tissue calibration may not be sufficient to identify the precise location and orientation of other types of tissue of interest, particularly if the tissue of interest is internal and/or if the tissue is especially sensitive. For example, if the needle 106*b* is to be used to puncture the spine of the patient 200, a very precise patient calibration is required.

In some embodiments, patient calibration is performed using another device or with an embodiment of the hand-held surgical tool tracking system 100. For example, but not limited to, the optical target 228 may be placed on the patient 200, preferably in proximity to the location of the tissue of interest. Then, an ultrasonagraphic system in accordance with U.S. Pat. Nos. 9,675,321 and 9,713,508, or an embodiment of the hand-held surgical tool tracking system 100 modified to incorporate the features of the above-identified ultrasonographic system, may be used to acquire one or more ultrasonic scans of the tissue of interest. Since the precise location and orientation of the ultrasonic sonic scanner is known (since it also has one or more discernable optical targets 102 on its surface), the precise location and orientation of the patient's tissue of interest with respect to the patient's detectable target 228 is determinable. Once patient tissue calibration has been completed, the surgical procedure may be initiated.

Yet another example of patient tissue calibration, the detectable target 228 may have a portion that is optically detectable, and a portion that is detectable in Xray images, CT images, fluoroscopy images, or the like. For example, one or more metal beads or the like may be at a known locations on the detectable target 102. Prior to the initiation of the surgical procedure, the detectable target 228 may be secured to the patient 200. Then, one or more images may be acquired of the patient 200. Since the tissue of interest and the detectable target 228 are discernable in the acquired image(s), then the precise location and orientation of the optical target 228 to the tissue of interest can be determined by the processor system 202.

As yet another example of patient tissue calibration, an MRI and/or CT system may be used to scan the patient. Since the tissue of interest and the optical target 228 are discernable in the acquired MRI and/or CT data, then the precise location and orientation of the detectable target 228 to the tissue of interest can be determined by the processor system 202.

Alternatively, or additionally, the patient tissue calibration process may occur on a real-time basis during the surgical procedure process. For example, sonogram images, Xray images, or the like can be acquired of the patient 200 (and their detectable target 228) during the surgical procedure. Embodiments of the hand-held surgical tool tracking system 100 may then calibrate in real-time. This calibration approach may be particularly desirable if the tissue of interest is moving during the surgical procedure. For example, the tissue of interest may be a beating heart of the patient 200 or the lungs of the patient 200 who is breathing during the surgical procedure.

Any suitable system for acquiring patient tissue calibration information during the surgical procedure is intended to be included within the scope of this disclosure and to be protected by the accompanying claims. Such patient tissue calibration can be acquired prior to, and/or during, the surgical procedure.

In practice, during the surgical procedure, the 2D or 3D model of the tissue of interest (an organ, bone, etc.) is retrieved from the tissue model data base 218. The retrieved tissue model of the patient 200 undergoing the current surgical procedure has been previously generated from an examination of the patient 200 prior to the current surgical procedure, and then stored in the tissue model data base 218. As the practitioner begins the surgical procedure, the hand-held surgical tool tracking system 100 determines the precise location and orientation of the hand-held surgical tool 104 in 3D space.

In an example embodiment, the image capture device 206 captures images in real tine that includes the optical targets 102*a*, 102*b* on the hand-held surgical tool 104 and the optical target 228 on the patient 200. The clock 222 may optionally provide time stamps to acquired images. The captured image data is then communicated from the image capture device 206 to the target tracker unit 208.

In some embodiments, a plurality of image capture devices 206 may be used to capture camera images from different viewpoints in a synchronized fashion. Here, the multiple image capture devices 206 provide concurrently captured camera images with the same time stamp.

The target tracker unit 208, for each acquired image, identifies the one or more optical targets 102 on the hand-held surgical tool 104 and the optical target 228 that have been placed on the surface of the body of the patient 200. The target tracker unit 208 then computes or determines the precise location and orientation of the optical targets 202 relative to the optical target 228 in 3D space for the indexed time. In some embodiments, the image data is analyzed to identify the particular hand-held surgical tool 104 that is currently being used by the practitioner.

In some embodiments, one or more of the detectable targets 102, 228 may not be optically detectable (since they may not be reflecting light in the visible spectrum). Another detecting device 206 is used to acquire image data from the detectable targets 102, 228 (that emit energy from other non-visible spectrums) to detect the precise location and orientation of the detectable targets 102. Then the target tracker unit 208 can determine the precise location and orientation of the detectable targets 202 relative to the detectable target 228 in the 3D space.

The image registration module 210 then receives the location and orientation information for the detectable targets 202 and 228. The image registration module 210 also retrieves the model data from the surgical tool model database 216 for the particular hand-held surgical tool 104 that is being used by the practitioner (and that has been optionally identified and/or verified in the captured images). The position of the hand-held surgical tool 104, and the position of the working end 106 of the hand-held surgical tool 104, is determined based upon the identified relative location of the detectable targets 102 and 228 in the acquired camera image and based on correlation with the retrieved model data of the corresponding hand-held surgical tool 104. Information corresponding to the precise location and orientation of the hand-held surgical tool 104 and its working end 106 in the 3D space is then communicated to the image processing algorithm module 212.

The image processing algorithm module 212 retrieves the previously generated and saved tissue model data of the tissue of interest of the patient 200 from the tissue model database 218. Preferably, the tissue model is based on the patient's tissue of interest during a previous tissue model generation process. When the tissue of interest is static (not moving, such as a bone or the like) during the surgical procedure, the tissue model data can be retrieved when the surgical procedure is initiated. Since the relative location and orientation of the hand-held surgical tool 104 (and its working end 106) relative to the detectable target 228 in the 3D space has been determined and, since the location of the tissue of interest relative to the detectable target 228 has been determined (during the patient calibration), the image processing algorithm module 212 may generate a real-time composite image that includes both an image of the hand-held surgical tool 104 and an image of the tissue of interest (as represented by the tissue model).

Data corresponding to the generated real-time composite image is communicated to the 3D/2D visualization module 214. The 3D/2D visualization module 214 then generates image data for presentation on a 3D display and/or a 2D display. In embodiments with the 3D/2D display 224, the composite image showing the precise location and orientation of the hand-held surgical tool 104, and in particular the working end 106 of the hand-held surgical tool 104 with respect to the tissue of interest (represented by the predetermined tissue model of the tissue of interest) is then rendered and presented on the display 224. The presented composite image may be either a 3D image or a 2D image depending upon the characteristics of the particular display 224.

In some embodiments of the hand-held surgical tool tracking system 100, the practitioner or another user may provide input to the 3D/2D visualization module 214 to adjust presentation of the composite image via the user input device 220. Any suitable type of under input device(s) 220 may be used in the various embodiments. In response to receiving the user input, the 3D/2D visualization module 214 may modify presentation of the composite image in accordance with the user input.

In some situations, the user input may be a request to zoom in on a particular location or region in the composite image. For example, the practitioner may wish to see a closeup image that presents a magnified image of the working end 106 of the hand-held surgical tool 104 and the tissue that is in proximity to the working end 106. Accordingly, the practitioner may be able to discern in greater detail and accuracy precisely where the working end 106 of the hand-held surgical tool 104 is currently at with respect to the tissue of interest.

As another exemplary situation, since the model of the tissue of interest is in 3D space and the precise location and orientation of the working end 106 of the hand-held surgical tool 104 is known in the 3D space, the practitioner or another user may wish to rotate the presented view of the composite image. For example, the practitioner may wish to examine a side view or a bottom of the composite image. The 3D/2D visualization module 214 may rotate the composite image so that the practitioner or another user is then presented the side view or the bottom view on the display 224.

Alternatively, or additionally, the composite image information can be communicated to the remote rendering and display system 204. The composite information that is rendered to present an image of the precise location and orientation of the hand-held surgical tool 104 and the tissue of interest can then be presented on a display of the remote rendering and display system 204. For example, the remote rendering and display system 204 may be a virtual reality system that employs a head set display device.

The practitioner or other user viewing the composite image on the display of the remote rendering and display system 204 may wish to adjust the view of the composite image. In some embodiments, information corresponding to the user's view request is communicated from the remote rendering and display system 204 to the 3D/2D visualization module 214. The 3D/2D visualization module 214 adjusts the composite view and then communicates the adjusted composite view to the remote rendering and display system 204 for presentation on the display. Alternatively, or additionally, the composite image data that is communicated to the remote rendering and display system 204 may include 3D model data of both the hand-held surgical tool 104 and the tissue of interest. The presented image on the display of the remote rendering and display system 204 may then be adjusted and presented by the remote rendering and display system 204.

It is appreciated by one skilled in the art that the processes of rendering, manipulating and presenting images based on 2D and 3D modelling technologies is well known in the arts. Such technologies are not described herein for brevity. All such technologies now known or later developed are considered to be within the scope of this disclosure and to be protected by the accompanying claims.

Figure 3:
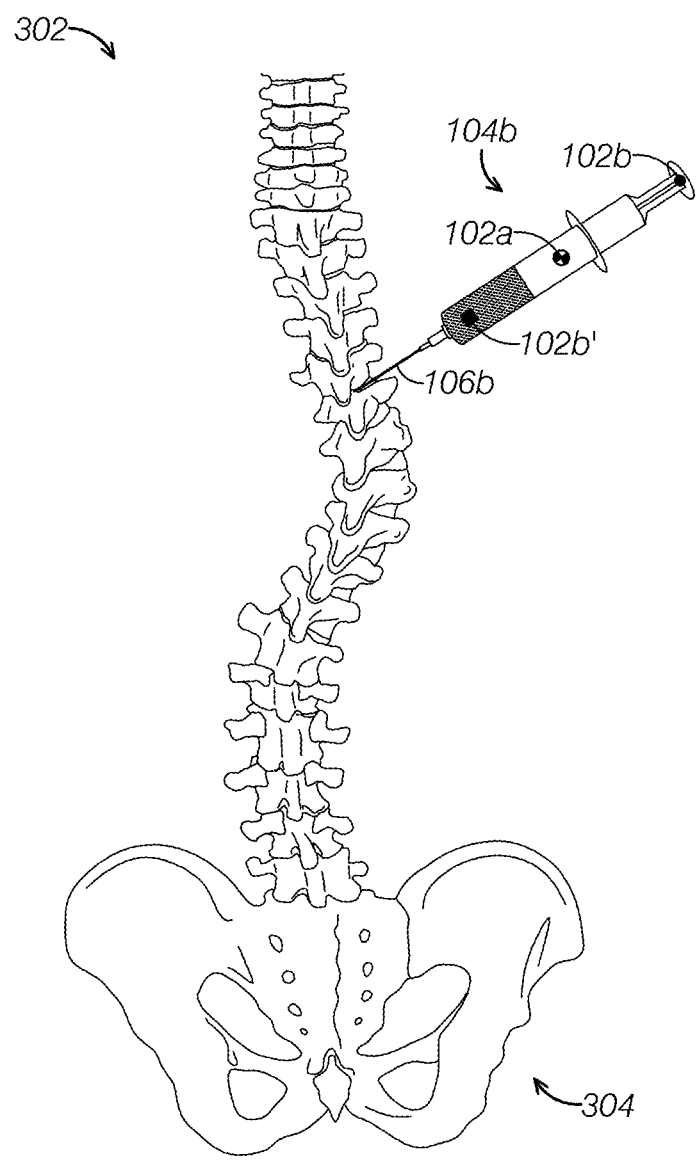
FIG. 3 is a conceptual illustration of a presented composite image showing the relative location of a spine of a patient and a hand-held surgical tool.

FIG. 3 is a conceptual illustration of a presented composite image 302 showing the relative location of a spine 304 of a patient 200 and a hand-held surgical tool 104. Here, the spine 304 is an example of a static tissue of interest that is not moving during the surgical procedure. The static tissue of interest might be other types of organs, such as a liver, a brain, a muscle or another bone. During some surgical procedures, a portion of the patient's body may be secured using a suitable securing device, such as, but not limited to, a clamp, a strap, or the like, that immobilizes the tissue of interest during the surgical procedure.

In this simplified conceptual example, the practitioner is inserting the needle 106*b* of the syringe 104*b* in between two vertebrae of the patient's spine, represented by the rendered spine model 304. One skilled in the art appreciates the delicate nature of this surgical procedure, and appreciates the importance of precisely locating and orienting the tip 106*b* of the syringe 104*b* for an injection or for tissue sampling. Typically, the practitioner is only viewing the skin surface of the patient 200, as illustrated in FIG. 2. Embodiments of the hand-held surgical tool tracking system 100 determine the precise location and orientation of the needle tip 106*b* relative to the patient's spine (based on the previously generated tissue model 304 of the patient's spine), and present a composite image 302 on a display that is viewable by the practitioner or another party. Further, movement of the needle tip 106*b* can be presented in the presented composite image 302 in real-time or near real-time. Here, the practitioner is able to view the needle tip 106*b* and the vertebrae of the spine as the needle tip 106*b* is puncturing the patient 200. Once the practitioner is satisfied with the precise location and orientation of the needle tip 106*b*, the practitioner can operate the syringe 104*b* to inject medicine into the spine or to retrieve a tissue sample from the spine.

Non-stationary tissue (moving tissue) presents a more complex issue of presenting the composite image of the tissue of interest and the hand-held surgical tool 104 on a real-time basis. For example, the tissue of interest may be a beating heart of the patient. Here, the previously generated tissue model of the tissue of interest may also include tissue movement characteristics. For example, if a heart is the tissue of interest, then the generated 3D model must have sufficient data to represent the beating of the heart. That is, the moving portions of the patient's heart must be visible in the presented composite image that represents the patient's beating heart and the precise location and orientation of the hand-held surgical tool 104.

Generation of 2D and 3D dynamic models representing moving objects is well understood in the arts. For brevity, such dynamic model generation is not described in detail herein. All such dynamic model generation systems and processes now known or later developed are intended to be included within the scope of this disclosure and to be protected by the accompanying claims.

Embodiments of the hand-held surgical tool tracking system 100 are configured to synchronize presentation of movement of the dynamic tissue model with actual movement of the patient's tissue in real-time. For example, the presented composite image will show a model of the patient's beating heart that corresponds to the actual beating of the heart. Similarly, other moving tissues will be synchronized with their dynamic tissue models.

In the various embodiments, a detector 232 that is configured to detect movement of tissue may be used to monitor movement of the tissue of interest during the surgical procedure. The detector 232 is communicatively coupled to the processor system 202 via a suitable wireless or wire-based connector. Tissue movement information is communicated from the detector 232 to the image processing algorithm module 212. The image processing algorithm module 212 synchronizes movement of the dynamic tissue model with the movement of the patient's tissue on a real-time or near real-time basis. Accordingly, the presented composite image accurately represents the movement of the tissue of interest.

In the situation where the tissue of interest is a beating heart, an audio detector such as a stethoscope or the like may be used to detect the beating of the patient's heart. As the heart beats are detected, information corresponding to the detected heart beating is communicated to the processor system 202. The movement of the dynamic model corresponding to the patient's heart may then be synchronized to the received heart beating information.

Detection of moving tissue is well known in the arts and is not described herein for brevity. Further, synchronization of the movement of dynamic models based on actual movement of the modelled object (here, the patient's tissue) is well known in the arts and is not described herein for brevity.

All such tissue movement detection and/or dynamic model generation systems and processes now known or later developed are intended to be included within the scope of this disclosure and to be protected by the accompanying claims.

Figure 4:
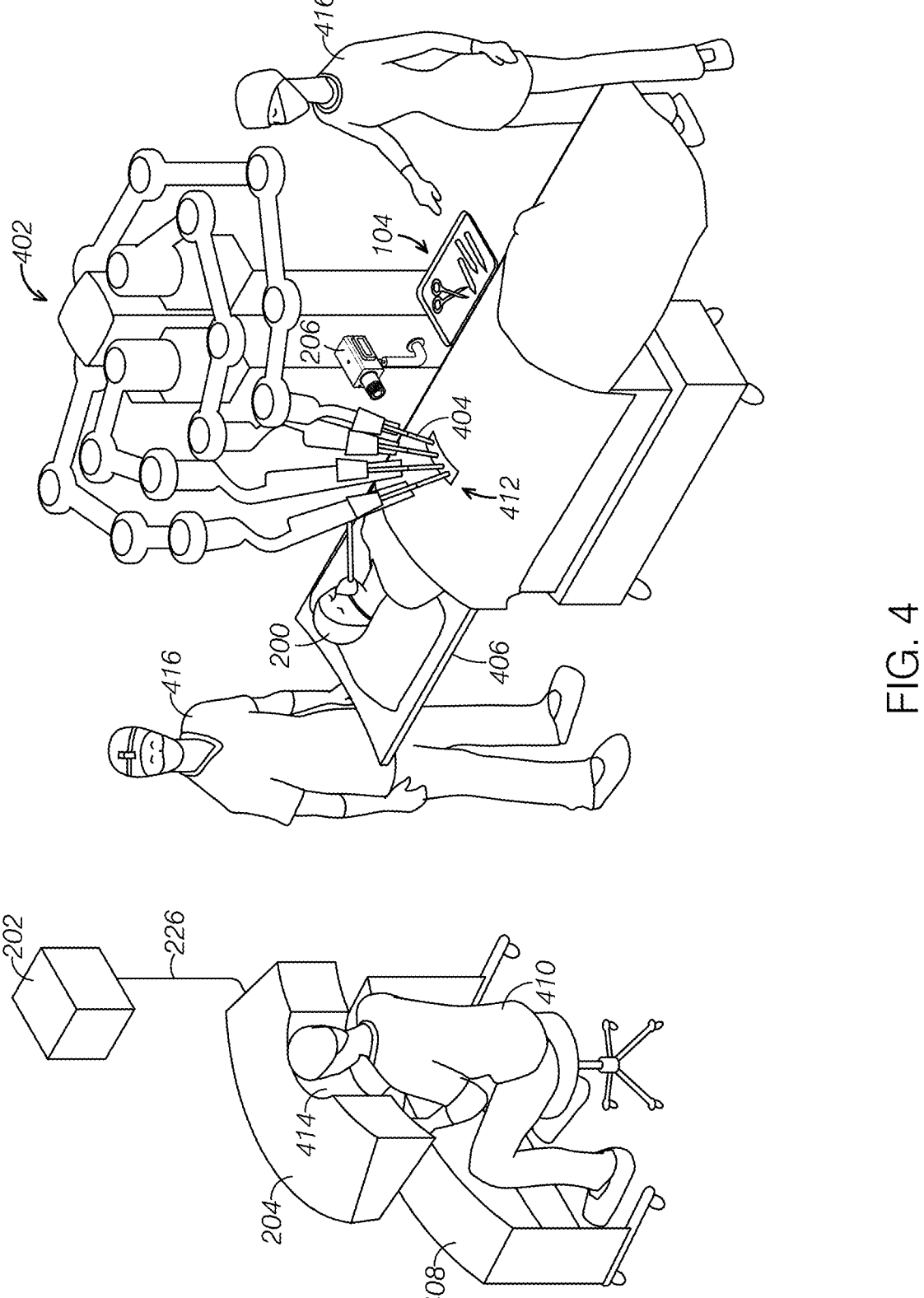
FIG. 4 is a conceptual diagram of an embodiment of the hand-held surgical tool tracking system and a robotic operation system cooperatively working together to generate a composite image that includes robotic tools and hand-held surgical tools.

FIG. 4 is a conceptual diagram of an embodiment of the hand-held surgical tool tracking system 100 and a robotic operation system 402 cooperatively working together to generate a composite image that includes robotic tools 404 and hand-held surgical tools 104. In this simplified hypothetical example, the patient 200 is laying on a surgical table 406 during a surgical procedure. A legacy robotic operation system 402 is manipulating one or more robotic tools 404 in accordance with instructions received from the robot controller 408 that are specified by the practitioner 410.

During the surgical procedure, the robotic operation system 402 determines the precise location and orientation of each of the robotic tools 404 as is known in the art of robotic tools. A graphical image of the tissue operating area 412 and the robotic tools 404 may be presented on a display 414 being viewed by the practitioner 410. Depending upon the robotic system, a 2D image of the operating area 412 and the robotic tools 404 may be presented on the display 414. Alternatively, or additionally, a 2D or 3D model of the tissue and the robotic tools 404 may be presented on the display 414.

On occasion, an assistant 416 may be required to assist or intervene in the surgical procedure by using one or more hand-held surgical tools 104. The robotic operation system 402, at best, can only obtain 2D image information showing the intervening hand-held surgical tools 104 as it are being used. It is not possible for the robotic operation system 402 to determine precise location and orientation of the intervening hand-held surgical tool 104 that is being used by the assistant.

However, the precise location and orientation of the intervening hand-held surgical tool 104 can be determined by embodiments of the hand-held surgical tool tracking system 100. Here, the image capture device 206 is positioned so as to capture images of the optically detectable targets 102 on the surface of the hand-held surgical tool 104. The 3D space known by the hand-held surgical tool tracking system 100 is the same as the 3D space known by the robotic operation system 402. Accordingly, image information presenting the precise location and orientation of the intervening hand-held surgical tool 104 can be generated by the hand-held surgical tool tracking system 100. This information may be communicated to the remote rendering and display system 204 for presentation of the display 214 along with concurrent presentation of graphical information generated by the robotic operation system 402. Accordingly, the practitioner 410 may concurrently view the robotic tools 404 being controlled by the robotic operation system 402 and the intervening hand-held surgical tool 104 being used by the assistant 416. If a 2D or 3D model of the tissue of interest in the operating area 412 is being presented on the display 414 (by either the hand-held surgical tool tracking system 100 or the robotic operation system 402), then the practitioner 410 is able to concurrently view the intervening hand-held surgical tool 104 and the robotic tools 404 in relation to the presented tissue model.

One skilled in the art appreciates that numerous robotic operation systems 402 are now known or will be developed in the future. Such robotic operation systems 402 may graphically present various information on a display 414 to the practitioner 410 who is operating the robotic operation system 402. These numerous robotic operation systems 402 are not described in detail herein for brevity. Further, integration of image information from multiple image generation sources into a single image is well known in the arts, and is not described herein in detail for brevity. Here, image informant generated by embodiments of the hand-held surgical tool tracking system 100 is integrated with image information generated by the robotic operation system 402 so that the practitioner 410 can appreciate the precise location and orientation of any intervening hand-held surgical tools 104 used during the surgical procedure. All such forms of robotic operation systems 402 know known or later developed, and all techniques of integrating image information know known or later developed, are considered to be within the scope of this disclosure and to be protected by the accompanying claims.

In some embodiments of the hand-held surgical tool tracking system 100, information corresponding to the generated and presented composite images (showing the tissue model and the hand-held surgical tools 104) may be saved into a local memory medium, such as the example surgical procedure history 230 (FIG. 2), and/or saved into remote memory medium (not shown). Preferably, the composite image information is time stamped. Accordingly, an interested party may later review and analyze the surgical procedure by viewing the saved composite images. The stored composite images may be individually viewed, or may be viewed as a video.

Determining precise location and orientation of hand-held surgical tools and other objects takes a discernable amount of time and is very computationally intensive for legacy object recognitions systems. Such legacy object recognition systems may not have sufficient computational capacity (processor system speed and or bandwidth) to determine precise location and orientation of an object in real-time or near real-time based on object recognition techniques alone. Embodiments of the hand-held surgical tool tracking system 100 address this problem by determining precise location and orientation of one or more detectable optical targets 102, and then correlating the detected optical targets 102 with known location of the optical targets of on a known model of the hand-held surgical tool 104.

As noted herein, detectable targets 102 may be active, such as by emitting infrared signals to the optical target, or passive, such as including retro-reflective markers affixed to some interaction device. Such active or passive detectable targets 102 are generically described herein as detectable targets for brevity, though such detectable targets 102 may not be optically detectable by an image capture device. Rather, the active or passive detectable targets 102 are detectable using another detecting device 206 or system 206.

It should be emphasized that the above-described embodiments of the hand-held surgical tool tracking system 100 are merely possible examples of implementations of the invention. Many variations and modifications may be made to the above-described embodiments. All such modifications and variations are intended to be included herein within the scope of this disclosure and protected by the following claims.

Furthermore, the disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower, or equal in scope to the original claims, are to be considered within the subject matter of the inventions described herein.

The inventions described in this application may be made by a variety of industrial processes, including by various mechanical, electrical, and pneumatic assembly techniques. Further, the inventions described herein may be used in industrial contexts, including surgical procedure endeavors.

The invention claimed is:

1. A surgical method, comprising:

capturing, using a first image capture device, first image data that includes both a first image portion indicating a first optical target residing on a hand-held surgical tool and a second image portion indicating a second optical target proximate to a patient, wherein the first optical target is located on the hand-held surgical tool at a first predefined target location, wherein the second optical target is located on the patient at a second predefined target location, and wherein a location relationship between a tissue of interest of the patient and the second predefined location of the second optical target is known;

determining a location of the first optical target and an orientation of the first optical target in a three dimensional (3D) space based on the first image portion of the first image data received only from the first image capture device;

retrieving hand-held surgical tool model data that represents the hand-held surgical tool, wherein the hand-held surgical tool model data comprises first optical target location model data that corresponds to the predefined location of the first optical target;

determining a current location of the hand-held surgical tool and a current orientation of the hand-held surgical tool in the 3D space based on the determined location of the first optical target and the determined orientation of the first optical target;

determining a location of the second optical target in the 3D space based on the second image portion of the first image data received only from the first image capture device; and determining a location of the tissue of interest in the 3D space based on the determined location of the second optical target on the patient.

2. The surgical method of claim 1, further comprising:

accessing tissue model data defining a tissue model corresponding to the tissue of interest of the patient, wherein the tissue model was previously generated from an examination of the patient prior to the current surgical procedure.

3. The surgical method of claim 2,
wherein the tissue model data was previously generated based on a series of acquired time indexed sonogram images.

4. The surgical method of claim 2, further comprising:
generating a composite image,
wherein the generated composite image concurrently presents a first graphical representation of the tissue of interest of the patient based on the tissue model and a second graphical representation of the hand-held surgical tool; and
presenting the generated composite image on a display.

5. The surgical method of claim 4,
wherein the hand-held surgical tool model data includes working end location model data that corresponds to a location of a working end of the hand-held surgical tool, and
wherein the working end of the hand-held surgical tool is disposed on a distal end of the hand-held surgical tool,
the method further comprising:
determining a location of the working end of the hand-held surgical tool and an orientation of the working end of the hand-held surgical tool based on the hand-held surgical tool model data.

6. The surgical method of claim 4, wherein the captured first image data is one of a plurality of time sequenced captured images of a video stream captured by the image capture device, the method further comprising:
continuously updating the generated image that is presented on the display using currently acquired first image data that is received in the video stream,
wherein the surgical team member viewing the display intuitively understands the current location of the hand-held surgical tool and the current orientation of the hand-held surgical tool with respect to the tissue of interest of the patient in real-time.

7. The surgical method of claim 2,
wherein the image capture device is a video camera.

8. The surgical method of claim 1,
wherein a third optical target is located on the hand-held surgical tool at a second predefined target location that is different from the first predefined target location,
wherein the hand-held surgical tool model data comprises third optical target location model data that corresponds to the predefined location of the third optical target,
the method further comprising:
determining a location of the third optical target the 3D space based only on the first image data, and based on the hand-held surgical tool model data,
wherein determining the current location of the hand-held surgical tool and the current orientation of the hand-held surgical tool in the 3D space is based on the determined location of the first optical target and the determined location of the third optical target.

9. The surgical method of claim 1,
wherein the first optical target is on a first surgical tool member of the hand-held surgical tool at the first predefined target location on the first surgical tool member of the hand-held surgical tool,
wherein the hand-held surgical tool includes a second surgical tool member that is coupled to the first surgical tool member,
wherein a third optical target is located on the second member of the hand-held surgical tool at a third predefined target location, and wherein the hand-held surgical tool model data further comprises third optical target location model data that corresponds to the predefined location of the third optical target,
the method further comprising:
determining a current location of the first member of the hand-held surgical tool and a current orientation of the first member of the hand-held surgical tool in the 3D space based on the determined location of the first optical target and the determined orientation of the first optical target;
determining a location of the third optical target and an orientation of the third optical target in the 3D space based on the first image data, and based on the hand-held surgical tool model data; and
determining a current location of the second member of the hand-held surgical tool and a current orientation of the second member of the hand-held surgical tool in the 3D space based on the determined location of the third optical target and the determined orientation of the third optical target.

10. The surgical method of claim 9,
wherein a first surgical tool member is disposed on a distal end of the first surgical tool member,
wherein a second surgical tool member is disposed on a distal end of the second surgical tool member,
wherein the first surgical tool member and the second surgical tool member cooperatively operate in a coordinated manner to perform a surgical operation on the tissue of the patient, and
wherein the method further comprises:
determining a current location of the first surgical tool member in the 3D space based on the determined location and orientation of the first surgical tool member, and based on the hand-held surgical tool model data; and
determining a current location of the second surgical tool member in the 3D space based on the determined location and orientation of the second surgical tool member, and based on the hand-held surgical tool model data.

11. The surgical method of claim 1,
wherein the first optical target is on a first surgical tool member of the hand-held surgical tool at the first predefined target location on the first surgical tool member of the hand-held surgical tool,
wherein a third optical target is on a first surgical tool member of the hand-held surgical tool at a third predefined target location on the first surgical tool member that is different from the first predefined target location,
wherein the hand-held surgical tool includes a second surgical tool member that is coupled to the first surgical tool member,
wherein a fourth optical target is located on the second member of the hand-held surgical tool at a fourth predefined target location,
wherein a fifth optical target is on a second surgical tool member of the hand-held surgical tool at a fifth predefined target location on the first surgical tool member that is different from the fourth predefined target location,
wherein the hand-held surgical tool model data further comprises:
third optical target location model data that corresponds to the predefined location of the third optical target;

fourth optical target location model data that corresponds to the predefined location of the fourth optical target; and fifth optical target location model data that corresponds to the predefined location of the fifth optical target, the method further comprising:

determining a location of the third optical target in the 3D space based only on the first image data, and based on the hand-held surgical tool model data;

determining a location of the fourth optical target in the 3D space based only on the first image data, and based on the hand-held surgical tool model data determining a location of the fifth optical target in the 3D space based on the first image data, and based on the hand-held surgical tool model data;

determining a current location of the first member of the hand-held surgical tool and a current orientation of the first member of the hand-held surgical tool in the 3D space based on the determined location of the first optical target and the determined location of the third optical target, and based on the hand-held surgical tool model data; and determining a current location of the second member of the hand-held surgical tool and a current orientation of the second member of the hand-held surgical tool in the 3D space based on the determined location of the fourth optical target and the determined location of the fifth optical target, and based on the hand-held surgical tool model data.

12. The surgical method of claim 1, wherein the first optical target is on a first surgical tool member of the hand-held surgical tool at the first predefined target location on the first surgical tool member of the hand-held surgical tool, wherein the hand-held surgical tool includes a second surgical tool member that is coupled to the first surgical tool member, wherein a third optical target is located on the second member of the hand-held surgical tool at a third predefined target location, wherein a fourth first optical target is located where the first surgical tool member is coupled to the second surgical tool member, wherein the hand-held surgical tool model data further comprises:

third optical target location model data that corresponds to the predefined location of the third optical target; and fourth optical target location model data that corresponds to the predefined location of the fourth optical target, the method further comprising:

determining a location of the third optical target in the 3D space based on the first image data, and based on the hand-held surgical tool model data;

determining a location of the fourth optical target in the 3D space based on the first image data, and based on the hand-held surgical tool model data;

determining a current location of the first member of the hand-held surgical tool and a current orientation of the first member of the hand-held surgical tool in the 3D space based on the determined location of the first optical target and the determined location of the fourth optical target, and based on the hand-held surgical tool model data; and determining a current location of the second member of the hand-held surgical tool and a current orientation of the second member of the hand-held surgical tool in the 3D space based on the determined location of the third optical target and the determined location of the fourth optical target, and based on the hand-held surgical tool model data.

13. The surgical method of claim 12, wherein a first surgical tool member is disposed on a distal end of the first surgical tool member wherein a second surgical tool member is disposed on a distal end of the second surgical tool member, wherein the first surgical tool member and the second surgical tool member cooperatively operate in a coordinated manner to perform a surgical operation on the tissue of the patient, and wherein the method further comprises:

determining a current location of the first surgical tool member and a current orientation of the first surgical tool member in the 3D space based on determined location and orientation of the first surgical tool member, and based on the hand-held surgical tool model data; and determining a current location of the second surgical tool member and a current orientation of the first surgical tool member in the 3D space based on determined location and orientation of the second surgical tool member, and based on the hand-held surgical tool model data.

14. The surgical method of claim 13, wherein the hand-held surgical tool is a surgical scissor, wherein the first surgical tool member is a first cutting edge of the surgical scissor, and wherein the second surgical tool member is a second cutting edge of the surgical scissor.

15. The surgical method of claim 13, wherein the manually manipulated surgical instrument is a surgical clamp, wherein the first surgical tool member is a first clamp of the surgical clamp, and wherein the second surgical tool member is a second clamp of the surgical clamp.

16. The surgical method of claim 1, wherein the hand-held surgical tool is a surgical scalpel with a surgical tool member that is a scalpel blade that is located at the distal end of the surgical scalpel.

17. The surgical method of claim 1, wherein the hand-held surgical tool is a syringe with a surgical tool member that is a needle located at a distal end of the syringe.

18. The surgical method of claim 1, wherein the hand-held surgical tool is a syringe with a surgical tool member that is a needle located at a distal end of the syringe, wherein the first optical target is on a plunger of the syringe, wherein a second optical target is on a barrel of the syringe, and wherein the hand-held surgical tool model data further comprises:

second optical target location model data that corresponds to the predefined location of the second optical target; and volume data corresponding to a volume of the barrel of the syringe, the method further comprising:

determining a change in location of the first optical target with respect to the location of the first optical target;

determining a change in a travel distance of a barrel seal located at the distal end of the plunger, wherein the travel distance equal a distance in the change of the location of the first optical target relative to the second optical target; and determining a volume defined within the barrel based on the determined travel distance of the barrel seal.

19. The surgical method of claim 1, wherein the surgical team member who is manually manipulating the manually manipulated surgical instrument is a first surgical team member that is viewing the rendered image on a first display, wherein a second surgical team member is controlling operation of a robotic surgery system that robotically manipulates a robotic surgical instrument, wherein the rendered image includes the first graphical representation of the tissue of interest of the patient, the second graphical representation of the manually manipulated surgical instrument being manipulated by the first surgical team member, and a third graphical representation of the robotic surgical instrument, wherein the method further comprises:

presenting the rendered image on the first display that is being viewed by the first surgical team member; and presenting the rendered image on a second display that is being viewed by the second surgical team member, and wherein the rendered image is concurrently presented on the first display to the first surgical team member and on the second display to the second surgical team member.

20. The surgical method of claim 19, further comprising:

receiving robotic surgical instrument model information from the robotic surgery system;

receiving robotic surgical instrument location information from the robotic surgery system that is based on a current location of the robotic surgical instrument; and receiving robotic surgical instrument orientation information from the robotic surgery system that is based on a current orientation of the robotic surgical instrument, wherein the rendered image, when presented on the first display and the second display, indicates the location and the orientation of the robotic surgical instrument relative to the location and the orientation of the manually manipulated surgical instrument, and indicates the location and the orientation of the robotic surgical instrument relative to the organ of interest.

\* \* \* \* \*